(12) United States Patent
Grimmelprez

(10) Patent No.: US 11,910,887 B2
(45) Date of Patent: Feb. 27, 2024

(54) FASTENING TAPE

(71) Applicant: APLIX, Le Cellier (FR)

(72) Inventor: Damien Jean Jacques Grimmelprez, Le Cellier (FR)

(73) Assignee: APLIX, Le Cellier (FR)

( * ) Notice: Subject to any disclaimer, the term of this patent is extended or adjusted under 35 U.S.C. 154(b) by 233 days.

(21) Appl. No.: 17/597,365

(22) PCT Filed: Jul. 10, 2020

(86) PCT No.: PCT/EP2020/069670
§ 371 (c)(1),
(2) Date: Jan. 4, 2022

(87) PCT Pub. No.: WO2021/009082
PCT Pub. Date: Jan. 21, 2021

(65) Prior Publication Data
US 2022/0265005 A1    Aug. 25, 2022

(30) Foreign Application Priority Data

Jul. 16, 2019 (FR) ........................................ 1907999

(51) Int. Cl.
*A44B 18/00*     (2006.01)
*B32B 5/02*      (2006.01)
(Continued)

(52) U.S. Cl.
CPC .......... *A44B 18/0015* (2013.01); *B32B 5/022* (2013.01); *B32B 7/12* (2013.01);
(Continued)

(58) Field of Classification Search
CPC .... A44B 18/0015; B32B 5/002; D04H 1/559; D04H 1/56; D04H 3/16; D10B 2509/026
See application file for complete search history.

(56) References Cited

U.S. PATENT DOCUMENTS

| | | | |
|---|---|---|---|
| 7,350,276 B2 * | 4/2008 | Minato | A44B 18/0061 264/210.1 |
| 8,819,902 B2 * | 9/2014 | Tuma | A44B 18/0007 24/442 |

(Continued)

FOREIGN PATENT DOCUMENTS

| | | |
|---|---|---|
| EP | 1878413 A1 | 1/2008 |
| WO | 2017187096 A1 | 11/2017 |

OTHER PUBLICATIONS

French Search Report issued in French Application FR1907999 dated Mar. 20, 2020 (2 pages).

(Continued)

*Primary Examiner* — Robert Sandy
(74) *Attorney, Agent, or Firm* — Bookoff McAndrews, PLLC

(57) ABSTRACT

A fastening tape having a substrate layer having a nonwoven layer with two opposite faces defining a first outer face and a second outer face of the substrate layer, and at least one fastening element provided on the first outer face of the substrate layer, the fastening tape being characterized in that the substrate layer presents an air permeability which is higher than 0 and lower than 30 l.m$^{-2}$.s$^{-1}$ as per ISO 9237 with a pressure of 200 Pa for a sample with a tested zone having a diameter of 8 mm.

10 Claims, 2 Drawing Sheets

(51) Int. Cl.
*B32B 7/12* (2006.01)
*D04H 1/56* (2006.01)
*D04H 3/16* (2006.01)
*D04H 1/559* (2012.01)

(52) U.S. Cl.
CPC .............. *D04H 1/559* (2013.01); *D04H 1/56* (2013.01); *D04H 3/16* (2013.01); *D10B 2509/026* (2013.01)

(56) References Cited

U.S. PATENT DOCUMENTS

| | | | |
|---|---|---|---|
| 10,016,022 B2* | 7/2018 | Nakada | B29C 43/52 |
| 2009/0288765 A1 | 11/2009 | Showole et al. | |
| 2015/0272790 A1* | 10/2015 | Fujisaki | A61F 13/5633 24/449 |

OTHER PUBLICATIONS

International Search Report issued in International Application PCT/EP2020/069670 dated Oct. 23, 2020 (3 pages).

* cited by examiner

[Fig. 1]
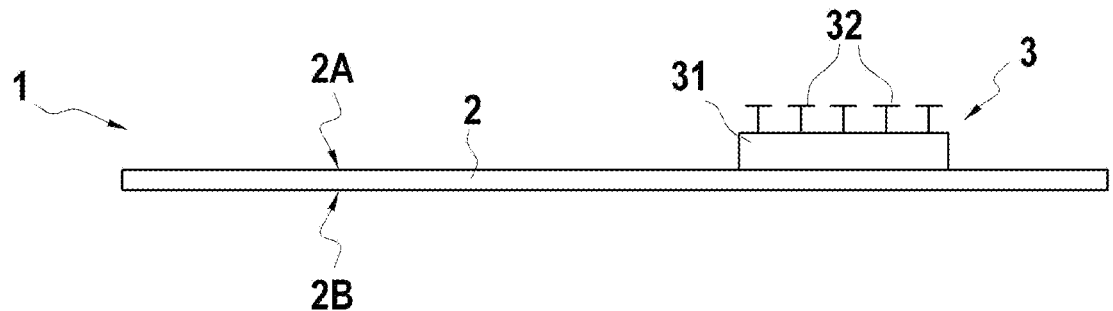
[Fig. 2]
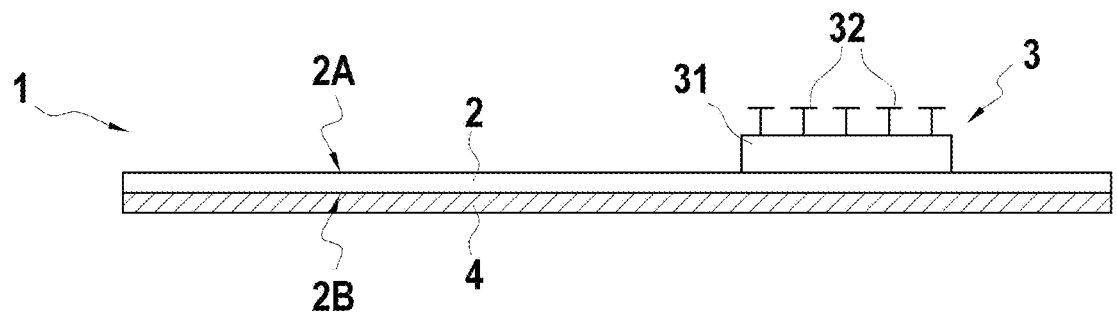
[Fig. 3]
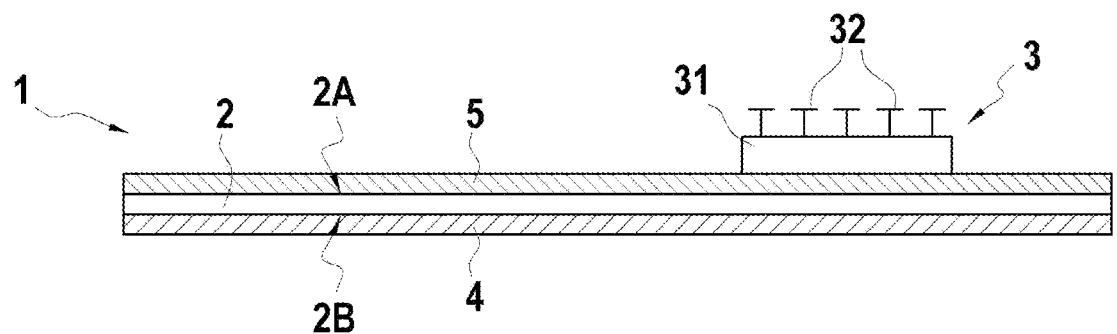

[Fig. 4]
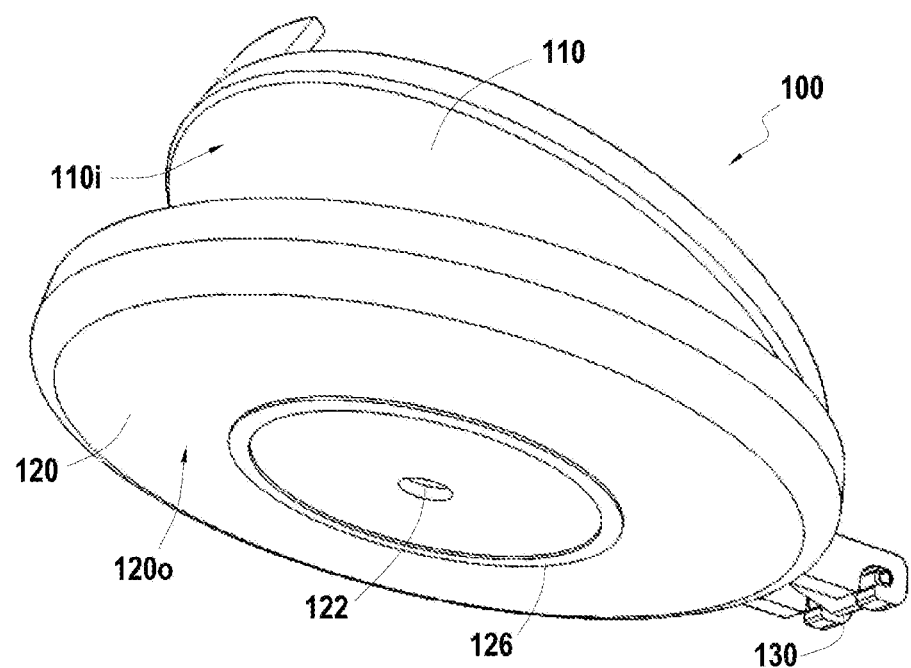
[Fig. 5]
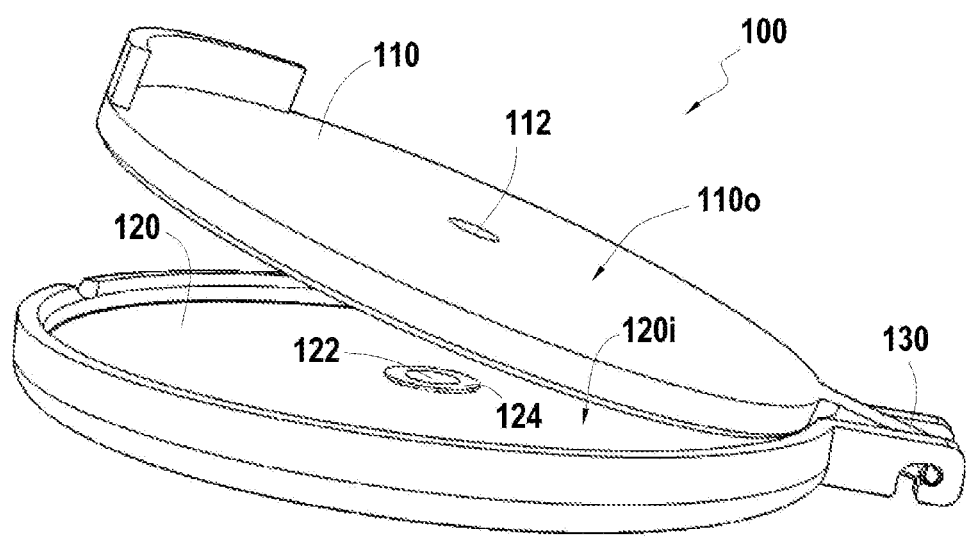

FASTENING TAPE

CROSS-REFERENCE TO RELATED APPLICATION(S)

This patent application is the U.S. National Stage entry under 35 U.S.C. § 371 of International Patent Application No. PCT/EP2020/069670, filed on Jul. 10, 2020, which claims the benefit of priority to French Patent Application No. 1907999, filed on Jul. 16, 2019. The '999 application is incorporated by reference herein in its entirety

TECHNICAL FIELD

The present disclosure relates to the field of fastening tapes that comprise fastening elements, which can be used for instance in the field of hygiene products or in the field of health and medical products among other possible applications.

STATE OF THE ART

Fastening tapes or hook tapes usually comprise a substrate layer made of nonwoven material, for instance of spunbond nonwoven material. This substrate is provided with a polypropylene coating on one face, and with a silicon coating on the other face. An adhesive layer is provided on a part of the polypropylene coating, and a hook element is provided on a part of the adhesive layer. The polypropylene coating aims at protecting the adhesive layer from the possible migration of the silicon coating through the nonwoven material.

However, the addition of such a polypropylene coating presents multiple drawbacks. Firstly, providing a polypropylene coating is costly, and the polypropylene layer must be subjected to a corona treatment in order to ensure the adhesion of the adhesive layer. Additionally, the polypropylene increases the stiffness of the tape and degrades the aspect of the product, which should both be avoided.

The present disclosure therefore aims at providing at least a partial solution to these issues.

PRESENTATION OF THE INVENTION

In order to at least partially address the aforementioned issues, the present disclosure relates to a fastening tape comprising a substrate layer comprising a nonwoven layer with two opposite faces defining a first outer face and a second outer face of the substrate layer, at least one fastening element provided on the first outer face of the substrate layer, the fastening tape being characterized in that the substrate presents an air permeability which is higher than 0 and lower than 30 $l.m^{-2}.s^{-1}$ or lower than 25 $l.m^{-2}.s^{-1}$ or lower than 15 $l.m^{-2}.s^{-1}$ or lower than 12.8 $l.m^{-2}.s^{-1}$ as per ISO 9237 with a pressure of 200 Pa for a sample with a tested zone having a diameter of 8 mm (equivalent to a circular surface of 50.27 $mm^2$), or an air permeability which is higher than 0 and lower than 1200 $l.m^{-2}.s^{-1}$ or lower than 1000 $l.m^{-2}.s^{-1}$ or lower than 600 $l.m^{-2}.s^{-1}$ or lower than 509 $l.m^{-2}.s^{-1}$ as per ISO 9237 with a pressure of 200 Pa for a sample with a tested zone having an area of 20 $cm^2$. Thus, with such features, the fastening tape presents properties of impermeability to air that are sufficient so that it can be gripped on assembly/production lines, for example for baby diapers and/or adult incontinence diapers.

According to an example embodiment, the substrate presents an air permeability which is higher than 0.1 and lower than 10 $l.m^{-2}.s^{-1}$ as per ISO 9237 with a pressure of 200 Pa for a sample with a tested zone having a diameter of 8 mm (equivalent to a circular surface of 50.27 $mm^2$), or an air permeability which is higher than 4 and lower than 398 $l.m^{-2}.s^{-1}$ as per ISO 9237 with a pressure of 200 Pa for a sample with a tested zone having an area of 20 $cm^2$.

According to an example embodiment, the nonwoven layer comprises fibres and/or filaments having a diameter of less than 0.02 mm or preferentially less than 0.01 mm, and more specifically of less than 0.005 mm.

According to an example embodiment, the product between the permeability of the substrate layer and the surface weight of the nonwoven layer is less than 1800 $g.l.m^{-4}.s^{-1}$ or is less than 1500 $g.l.m^{-4}.s^{-1}$ or is less than 800 $g.l.m^{-4}.s^{-1}$ and in particular less than 400 $g.l.m^{-4}.s^{-1}$, the air permeability being measured as per ISO 9237 with a pressure of 200 Pa for a sample with tested zone having a diameter of 8 mm. The product between the permeability of the substrate layer and the weight of the nonwoven layer is also typically higher than zero.

According to an example embodiment, the nonwoven layer comprises at least one layer of meltblown material and/or at least one layer of spunbond material. The nonwoven layer can then comprise at least one layer of meltblown material arranged between at least two layers of spunbond material.

According to an example embodiment, the second outer face of the substrate layer comprises a silicone coating.

According to an example embodiment, an adhesive layer is provided on the first outer face of the substrate layer.

According to an example embodiment, the fastening element comprises at least a hook and/or a stem, in particular a plurality of hooks and/or a plurality of stems.

According to one example, the height of the retaining elements is between 5 and 5000 micrometers, more particularly between 5 and 2000 micrometers, or more particularly between 20 and 800 micrometers, the height being measured in a direction perpendicular to the upper surface of the base.

According to an example embodiment, the fastening element is bonded to the first outer face of the substrate layer by direct lamination. According to an example, the fastening element can comprise a base and at least a hook and/or a stem, in particular a plurality of hooks and/or a plurality of stems projecting from one face of the base. Some portions of the fibres and/or filaments of the substrate layer as nonwoven can be encapsulated into the base and/or some fibres and/or filaments extending directly from another (the opposite) face of the base.

According to an example embodiment, the fastening element is as described in the document WO2017187096 A1 that is incorporated by reference and to which one can refer when considering the present disclosure.

According to an example embodiment, the substrate layer has a basis weight between 5 gsm and 100 gsm, in particular between 25 gsm and 65 gsm.

BRIEF INTRODUCTION OF THE DRAWINGS

The present disclosure and its advantages will be best understood in view of the enclosed drawings, which are listed hereafter.

FIG. 1 is an example of a fastening tape according to an aspect of the invention.

FIG. 2 is another example of a fastening tape according to an aspect of the invention.

FIG. 3 is another example of a fastening tape according to an aspect of the invention.

FIG. 4 is an example of adapter to measure the air permeability of a fastening tape.

FIG. 5 is another view of an example of adapter to measure the air permeability of a fastening tape.

In all the figures, the elements in common are designated by identical numeral references.

DESCRIPTION OF THE EMBODIMENTS OF THE INVENTION

A fastening tape according to an example embodiment of the present disclosure is represented in FIG. 1.

The fastening tape 1 presented in FIG. 1 comprises: a substrate layer 2, and at least one fastening element 3 provided on one outer face of the substrate layer 2.

The substrate layer 2 is for instance made out of a nonwoven layer which is in the shape of a tape, and presents two opposite faces defining a first outer face 2A and a second outer face 2B. In the illustrated example of FIG. 1, the fastening element 3 is arranged on the first outer face 2A of the substrate layer 2.

The fastening element 3 can for instance comprise a base 31 and at least one retaining element 32 such as hooks and/or stem, or more generally elements that comprise a stem extending from the base, and a head arranged on the top of the stem, the head being configured to cooperate with either another similar retaining element 32 and/or with loops and/or with nonwoven material to define a releasable fastening.

A nonwoven is a product obtained by forming a web of fibres and/or filaments that have been consolidated. Consolidation can be mechanical, chemical or thermal and results in the presence of a bond between the fibres and/or filaments. This consolidation can be direct, i. e. made directly between the fibres and/or filaments by welding, or it can be indirect, i. e. through an intermediate layer between the fibres and/or filaments, for example an adhesive layer or a binder layer. The term nonwoven refers to a ribbon-shaped structure or web of fibres and/or filaments that are intertwined in a non-uniform, irregular or random manner. A nonwoven can have a single layer structure or a multi-layer structure. A non-woven fabric can also be combined with another material to form a laminate. A nonwoven can be made from different synthetic and/or natural materials. Examples of natural materials are cellulose fibres, such as cotton, jute, flax and the like, and may also include reprocessed cellulose fibres, such as rayon or viscose. Natural fibres for a non-woven material can be prepared using various processes such as carding. Examples of synthetic materials include, but are not limited to, synthetic plastic polymers, which are known to form fibres that include, but are not limited to, polyolefins, e. g. polyethylene, polypropylene, polybutylene and similar; polyamide, e. g. polyamide 6, polyamide 6.6, polyamide 10, polyamide 12 and the like; polyesters, for example polyethylene teraphthalates, polybutylenes terephthalates, polylactic acids and the like, polycarbonates, polystyrenes, thermoplastic elastomers, polymeric vinyls, polyurethanes and mixtures and copolymers thereof. For example, the nonwoven can be a nonwoven such as Spunbond, Spunmelt, thermally bonded carded, SMS, SMMS, SS, SSS, SSMMS, SSMMS, SSMMMS, Air through or other. These examples are given without limitation. We can also use nonwoven having a nanofibers layer for example produced by process of melt-blown technology or electrospinning technology.

The substrate layer 2 presents an air permeability which is higher than 0 and lower than 30 $l.m^{-2}.s^{-1}$, or more precisely lower than 25 $l.m^{-2}.s^{-1}$, or for instance lower than 15 $l.m^{-2}.s^{-1}$, or more precisely lower than 12.8 $l.m^{-2}.s^{-1}$ as per the measurement method defined in French and European regulation NF EN ISO 9237 published in Aug. 1995, ISSN 0335-3931, with a measurement surface which is in the shape of a disc with a diameter of 8 mm and a pressure of 200 Pa.

The tested area is reduced to a disc with a diameter of 8 mm (i.e. an area of roughly 0.50 $cm^2$) due to some of the expected applications of the fastening tape 1, for instance on diapers, which will lead to portions of fastening tape 1 having small dimensions. FIGS. 4 and 5 represent an example of an adapter 100 to perform the measurements defined in French and European regulation NF EN ISO 9237 on a sample with a tested area having a diameter of 8 mm.

The adapter 100 as presented comprises two parts: an upper part 110 and a lower part 120 which are connected by a hinge 130. The upper part 110 presents an inner face 110i and an outer face 110o. The lower part 120 presents an inner face 120i and an outer face 120o. The inner face 110i of the upper part is adapted to come in contact with the inner face 120i of the lower part 120 when the adapter is closed. The upper part 110 and the lower part 120 each present a through opening, respectively 112 and 122. The openings 112 and 122 each present a circular shape with a diameter of 8 mm, and are aligned with each other, to allow a flow of air or fluid to go through the adapter 100. The opening of the lower part 120 is surrounded by a sealing ring 124, which is arranged on the face of the lower part 120 which faces the upper part 110, i.e. on the inner face 120i of the lower part 120. This sealing ring 124 ensures an air-tight sealing when the upper part 110 is brought in contact with the lower part 120 of the adapter 100. The sample product to be tested is positioned between the upper part 110 and the lower part 120 of the adapter 100, in front of their respective openings 112 and 122, and then the upper part 110 is closed on the lower part 120.

It is understood that the sealing ring 124 could be arranged on the inner face of the upper part, around the opening 112 made in the upper part 110 instead of or in addition to the sealing ring provided on the inner face 120i around the opening made in the lower part 120.

The outer face 120o of the lower part 120 can be provided with a sealing ring 126, which can for instance facilitate the measurement of the flow that goes through the adapter 100, i.e. the flow that goes through the product to be tested.

If the substrate layer 2 is provided with an adhesive layer and/or a silicon layer (see the embodiments described hereafter), then these layers are removed before the measurement of air permeability of the substrate layer 2, for instance using acetone or ethyl acetate.

When performing the measurement according to European regulation NF EN ISO 9237 with a tested area having an area of 20 $cm^2$ as per the suggested parameters of the regulation, and with a pressure of 200 Pa, then the substrate layer 2 presents an air permeability which is higher than 0 and lower than 1200 $l.m^{-2}.s^{-1}$, or lower than 1000 $l.m^{-2}.s^{-1}$, or lower than 600 $l.m^{-2}.s^{-1}$, or typically lower than 500 $l.m^{-2}.s^{-1}$. The applicant has determined that there is a linear relationship between the results obtained with a tested area with a diameter of 8 mm and with a tested area with a surface of 20 $cm^2$, such that the two measurement methods are equivalent.

The substrate layer 2 as presented therefore presents an air permeability which is higher than zero, but which is within a limited range. While this does not fully prevent air from going through the substrate layer 2, a value of air permeability within such a range enables to prevent the migration of a material such as a coating that would be provided on one side of the substrate layer 2 to migrate through the substrate layer 2 to reach the other side of the substrate layer 2.

The air permeability properties of the substrate layer 2 are obtained through the structure of the substrate layer 2, without requiring the addition of a supplementary layer such as an additional coating. This therefore suppresses the drawbacks of the known articles which comprise a coating such as a polypropylene coating provided on the face of the substrate layer 2 on which the fastening elements 3 are arranged, to protect the fastening elements 3 from a migration of a coating material that can be provided on the opposite side of the substrate layer 2. The fastening tape 1 can therefore prevent the migration of the coating material, while still presenting an air permeability higher than zero, without requiring the addition of a supplementary layer such as a polypropylene coating which decreases the flexibility of the fastening tape 1 and is costly and complex to achieve.

The substrate layer 2 can be made of nonwoven material which comprises fibres and/or filaments having a diameter of less than 0.02 mm or more specifically less than 0.01 mm, or more specifically of less than 0.005 mm.

In an example embodiment, the nonwoven layer 2 can comprise at least one layer of meltblown and/or spunbond material. The nonwoven layer 2 can then optionally comprise at least one layer of meltblown material arranged between at least two layers of spunbond material. By using a spunbond nonwoven layer as outside layer, we can obtain a nonwoven layer which is softer than a nonwoven layer having as outside layer as a meltblown layer. By using a spunbond nonwoven layer as outside layer, we can obtain a nonwoven layer which has a improved anchoring capacity on the two faces of the nonwoven, for example for a better anchoring between the base of the fastener and the substrate as nonwoven. Additionally, the permeability of the product decreases as the number of layers of meltblown material increases.

According to an example embodiment of the present disclosure, which is depicted in FIG. 2, the substrate layer can have two layers of spunbond with one of the two layers of spunbond having a fiber/filament size diameter which can be between 1 micrometer and 20 micrometers or for instance between 12 micrometers and 19 micrometers, and a meltblown layer having a fiber/filament size diameter which can be between 1 micrometer and 10 micrometers, or for instance between 1 micrometer and 5 micrometers. The substrate layer can also have layers (N) of nanofibers having a fiber/filament size diameter less than 1 micrometer, in some case between 0.05 micrometer and 1 micrometer (typically strictly less than 1 micrometer).

According to an example embodiment of the present disclosure, which is depicted in FIG. 2, the substrate layer can be selected from the following list Spunbond, Spunmelt, SMS, SMMS, SS, SSS, SSMMS, SSMMS, SSMMMS, or another combination of Spunbond (S) and Meltblown (M) layer or SMNMS or another combination of Spunbond (S) and Meltblown (M) and Nanofibers (N).

According to an example embodiment of the present disclosure, which is depicted in FIG. 2, the substrate layer can be a combination of sub-layers, for example having two, three, four, five, six or seven sub-layers, for example spunbond sub-layers, that differ in fiber/filament densities and/or fiber/filament diameters and/or sub-layer thicknesses and/or fiber/filament raw materials and/or fiber/filament kinds (side by side, eccentric, core/sheath) and/or fiber/filament weights. In particular, the substrate layer comprises only spunbond sub-layers.

According to an example embodiment of the present disclosure which is depicted in FIG. 2, the second opposite face 2B of the substrate layer 2 (or more generally, the face of the substrate layer 2 which is not provided with the fastening element 3) can be provided with a silicone coating 4 so as to form a release coating for the substrate layer 2.

In an example embodiment, the substrate layer 2 has a basis weight which is in the range of 5 gsm to 100 gsm, the basis weight being the weight of the substrate layer 2 prior to the addition of other elements such as the fastening element 3 or optional coatings or layers on the substrate layer 2.

In an example embodiment, the product between the permeability of the substrate layer 2 and the surface weight of the substrate layer is less than 1800 $g.l.m^{-4}.s^{-1}$, in particular less than 1500 $g.l.m^{-4}.s^{-1}$, or for instance less than 800 $g.l.m^{-4}.s^{-1}$ and in particular less than 400 $g.l.m^{-4}.s^{-1}$, the air permeability being measured as per ISO 9237 with a pressure of 200 Pa for a sample with tested zone having a diameter of 8 mm. The product between the permeability of the substrate layer and the weight of the substrate layer is also typically higher than zero.

The reduced value of air permeability of the substrate layer 2 therefore prevents the silicone of this silicone coating 4 from migrating through the substrate layer 2 to reach the opposite side of the substrate layer 2 which comprises the fastening elements 3.

According to an example embodiment as depicted in FIG. 3, the first outer face 2A of the substrate layer 2 can be provided with an adhesive layer 5, which is then provided between the first outer face 2A of the substrate layer 2 and the fastening elements 3 and ensures the bonding of the fastening elements 3 to the substrate layer 2.

In such an embodiment, the reduced value of air permeability of the substrate layer 2 therefore prevents the silicone of the optional silicone coating 4 from migrating through the substrate layer 2 to reach the adhesive layer 5 on the opposite side of the substrate layer 2.

In an alternative embodiment, the fastening element 3 can be bonded to the substrate layer 2 by direct lamination. In such an embodiment, the adhesive layer 5, if any, can be provided on areas of the substrate layer 2 which are distinct from the area where the fastening element 3 is arranged.

Table 1 hereafter provides different examples of samples that were tested according to ISO 9237, and illustrates examples of substrate that can be used in order to provide a fastening tape as per the present disclosure.

TABLE 1

| Sample | Type | M1 | M2 | M2/M1 |
|---|---|---|---|---|
| A | SMS | 323.8 | 8.304 | 2.56 |
| B | SMS | 316.8 | 8.408 | 2.65 |
| C | SMS | 375.4 | 11.52 | 3.07 |
| D | SMS | 491.2 | 12.82 | 2.61 |
| E | SMS | 400.2 | 9.728 | 2.43 |
| F | SMS | 374.4 | 9.734 | 2.60 |
| G | SB | 1598 | 40.48 | 2.53 |
| H | SB | 1084 | 24.06 | 2.22 |

Sample A: SMS substrate manufactured by FITESA under the reference NA3SB060 with 60% wt meltblown layer having a basis weight of 60 gsm.

Sample B: SMS substrate manufactured by FITESA under the reference NA3SB060 with 60% wt meltblown layer with a 3.5 gsm silicon layer having a basis weight of 60 gsm.

Sample C: SMS substrate manufactured by PEGATEX under the reference SMS 65 GSM ON LINE having a basis weight of 65 gsm.

Sample D: SMS substrate manufactured by FITESA under the reference PHOBIC 60 GSM IC3EW 100 060 NN F having a basis weight of 60 gsm.

Sample E: SMS substrate manufactured by DOUNOR under the reference HYMELT PPSM 60 W O S PHOBIC having a basis weight of 60 gsm.

Sample F: SMS substrate manufactured by UNION under the reference D6003 PHW having a basis weight of 60 gsm.

Sample G: Spunbond substrate manufactured by TEXBOND under the reference NT AX SA 50A 50 gsm having a basis weight of 50 gsm.

Sample H: Spunbond substrate manufactured by UNION under the reference S6000 PHW having a basis weight of 60 gsm.

M1 is the permeability of the substrate in $l/m^2/s$ as measured per the ISO 9237 regulation with a pressure of 200 Pa for a tested sample with an area of 20 $cm^2$.

M2 is the permeability of the substrate in $l/m^2/s$ as measured per the ISO 9237 regulation with a pressure of 200 Pa for a tested sample with a diameter of 8 mm.

M2/M1 is the ratio of the value of M2 divided by the value of M1 in percentage.

In the examples listed in Table 1, samples A, B, C, D, E, F and H are within the scope of the present disclosure. Sample G however, is outside of the scope of the present disclosure, as its permeability is too high.

The permeability values in Table 1 were obtained using the FX 3300 Air Permeability Tester.

The fastening tape of the present disclosure can be used for instance for an absorbent article, such as a diaper or a product for adult incontinence.

Even though the present disclosure has been disclosed in relation to specific embodiments, it is to be understood that modifications can be made to these examples without departing from the scope of the invention as defined by the claims. In particular, features from the different embodiments that have been presented and/or illustrated can be taken individually and combined in additional embodiments. The present disclosure and drawings therefore have to be interpreted in a non-limiting way.

It is also to be understood that all the features that have been described in relation to a device can be transposed individually or in combination to a method or a process, and in reciprocity, that all the features that have been described in relation to a method or process can be transposed individually or in combination to a device.

The invention claimed is:

1. A fastening tape comprising:
   a substrate layer comprising a nonwoven layer with two opposite faces defining a first outer face and a second outer face of the substrate layer, and
   at least one fastening element provided on the first outer face of the substrate layer,
   the fastening tape being characterized in that the substrate layer presents an air permeability which is higher than 0 and lower than 30 $l.m^{-2}.s-1$ as per ISO 9237 with a pressure of 200 Pa for a sample with a tested zone having a diameter of 8 mm.

2. A fastening tape according to claim 1, wherein the nonwoven layer comprises fibres and/or filaments having a diameter of less than 0.02 mm.

3. A fastening tape {-1-} according to claim 1, wherein the product between the permeability of the substrate layer and the surface weight of the nonwoven layer is less than 800 $g.l.m-4.s$ 1 with a pressure of 200 Pa for a sample with tested zone having a diameter of 8 mm.

4. A fastening tape according to claim 1, wherein the nonwoven layer comprises at least one layer of meltblown material and/or at least one layer of spunbond material.

5. A fastening tape according to claim 4, wherein the nonwoven layer comprises at least one layer of meltblown material arranged between at least two layers of spunbond material.

6. A fastening tape according to claim 1, wherein the second outer face of the substrate layer comprises a silicone coating.

7. A fastening tape according to claim 1, wherein an adhesive layer is provided on the first outer face of the substrate layer.

8. A fastening tape according to claim 1, wherein the fastening element comprises at least a hook and/or a stem.

9. A fastening tape according to claim 1, wherein the fastening element is bonded to the first outer face of the substrate layer by direct lamination.

10. A fastening tape according to claim 1 wherein the substrate layer has a basis weight between 5 gsm and 100 gsm.

* * * * *